United States Patent [19]
Childers et al.

[11] Patent Number: 5,876,664
[45] Date of Patent: Mar. 2, 1999

[54] CONTINUOUS-OPERATION, CLOSED LOOP DECONTAMINATION SYSTEM AND METHOD

[75] Inventors: Robert W. Childers, New Port Richey, Fla.; Stephen G. Geist, Raleigh; Paul A. Steen, Apex, both of N.C.

[73] Assignee: American Sterilizer Company, Mentor, Ohio

[21] Appl. No.: 664,985

[22] Filed: Jun. 14, 1996

Related U.S. Application Data

[63] Continuation-in-part of Ser. No. 664,980, Jun. 14, 1996.

[51] Int. Cl.$^6$ .............................. G05D 23/00; A61L 9/00; B01J 7/00
[52] U.S. Cl. ........................... 422/28; 422/109; 422/305; 422/306
[58] Field of Search ................................. 422/8, 109, 224, 422/305, 194, 306, 28, 32, 33; 423/350, 118.1

[56] References Cited

U.S. PATENT DOCUMENTS

| | | |
|---|---|---|
| 4,302,177 | 11/1981 | Fankhanel .................................. 431/11 |
| 4,435,194 | 3/1984 | Picard et al. . |
| 4,509,505 | 4/1985 | Mercey et al. . |
| 4,898,713 | 2/1990 | Picard . |
| 4,909,999 | 3/1990 | Cummings et al. . |
| 4,956,145 | 9/1990 | Cummings et al. . |
| 4,992,247 | 2/1991 | Foti . |
| 5,173,258 | 12/1992 | Childers . |
| 5,258,162 | 11/1993 | Andersson et al. . |
| 5,445,792 | 8/1995 | Rickloff et al. . |
| 5,508,009 | 4/1996 | Rickloff et al. . |

FOREIGN PATENT DOCUMENTS

| | | |
|---|---|---|
| 298 694 | 1/1989 | European Pat. Off. . |
| 774263 | 5/1997 | European Pat. Off. . |
| WO 88/04939 | 7/1988 | WIPO . |
| WO 89/06140 | 7/1989 | WIPO . |
| 91/05573 | 5/1991 | WIPO . |
| WO 91/05573 | 5/1991 | WIPO . |

*Primary Examiner*—Lynette F. Smith
*Assistant Examiner*—Brett Nelson
*Attorney, Agent, or Firm*—Fay, Sharpe, Beall, Fagan, Minnich & McKee

[57] ABSTRACT

The invention provides a method and apparatus for minimizing heat degradation of a vapor decontaminant in a vaporizer by selectively operating a plurality of vaporizer heaters to provide a decreasing heat gradient through the vaporizer. A method and apparatus are also provided for selectively operating a plurality of preheaters, in series, for preheating a carrier gas entering a vaporizer in a flow-through decontamination system, and for maintaining a predetermined carrier gas temperature. A further method and apparatus are provided for fine-tuning chamber pressure in a high flow rate closed-loop flow-through vapor phase decontamination system.

18 Claims, 6 Drawing Sheets

CONTINUOUS-OPERATION, CLOSED LOOP DECONTAMINATION SYSTEM AND METHOD

This application is a continuation-in-part of U.S. application Ser. No. 08/664,980 filed Jun. 14, 1996, pending, that claims the benefit of U.S. Provisional Application No. 60/000,321, filed Jun. 15, 1995.

FIELD OF THE INVENTION

The present invention relates generally to a system and method of vapor-phase decontamination, and more particularly to a flow-through system and method of decontamination using a vapor phase decontaminant.

BACKGROUND OF THE INVENTION

Reusable medical, pharmaceutical, and biological instruments are generally sterilized before each use. Additionally, reusable containers employed in medical, pharmaceutical, and biological applications, such as glove boxes and incubators, are generally sterilized before each use. In facilities and applications where these types of instruments and containers are used several times a day, it is important to achieve sterilization efficiently and economically.

Several different methods have been developed for delivering a vapor phase sterilant to an enclosure or chamber for sterilizing the load (e.g., medical instruments) or interior thereof. In one option, the "deep vacuum" approach, a deep vacuum is used to pull liquid sterilant into a heated vaporizer; once vaporized, the sterilant is propelled by its vapor pressure into an evacuated and sealed chamber. In another option, the "flow-through" approach, vaporized sterilant is mixed with a flow of carrier gas that serves to deliver the sterilant into, through and out of the chamber, which may be at slightly negative or positive pressure.

In addition, methods have been developed for optimizing vapor phase sterilization in a deep vacuum and/or flow-through system. U.S. Pat. No. 4,956,145 discloses a deep vacuum method of vapor phase sterilization in which a predetermined concentration of hydrogen peroxide sterilant is maintained in an evacuated, sealed chamber. The amount of sterilant injected into the chamber is regulated or adjusted to account for the decomposition of hydrogen peroxide sterilant vapor into water and oxygen in the closed system over time. A different approach is disclosed in U.S. Pat. Nos. 5,445,792 and 5,508,009, incorporated by reference herein, wherein a predetermined percent saturation is maintained in an open, flow-through sterilization. The rate of hydrogen peroxide vapor injection into a carrier gas is regulated or adjusted in response to predetermined characteristics of the carrier gas.

Also, several systems and apparatus have been developed for conducting vapor phase sterilization. An open flow-through system designed to handle the disposition of residual sterilant vapors is disclosed in U.S. Pat. No. 4,909,999 and is incorporated by reference herein. That system can be integrally associated with or releasably connected to a sealable container.

U.S. Pat. No. 5,173,258, which is incorporated by reference herein, discloses another flow-through system in which vapor phase hydrogen peroxide is introduced into a recirculating, closed flow of carrier gas. The hydrogen peroxide vapor is introduced and maintained at a predetermined concentration selected to optimize the sterilization cycle. The system includes a dryer to dehumidify the recirculating flow, preferably to at least about 10% relative humidity, and thereby prevent moisture build-up resulting from the decomposition of hydrogen peroxide vapor over time. By eliminating moisture build-up, the system can maintain the sterilization chamber at higher concentrations of vapor phase hydrogen peroxide sterilant for longer periods of time (i.e., the predried gas will accept more of the sterilant vapor). Further, to avoid condensation of the sterilant, the relative humidity in the chamber is preferably reduced (e.g., to at least about 10%) prior to introducing sterilant vapor. After decontamination is complete, the enclosure may be rehumidified or conditioned if desired for the selected application.

The foregoing methods and systems are effective at sterilization and/or provide an enhanced sterilization cycle. However, each of the aforementioned flow-through systems employ a comparatively low carrier gas or air flow rate of approximately 12–20 standard cubic feet per minute (SCFM) and a low liquid sterilant injection rate into the vaporizer. If higher carrier gas flow rates of up to 40–70 SCFM or more are employed, an increase in the amount of liquid sterilant injected into the vaporizer is required to maintain a predetermined vapor concentration. The combination of increased liquid and increased flow rate may have the result that not all of the liquid particles come into contact with the heated vaporizer wall and the liquid is not completely vaporized. Further, when employing a vapor sterilant that is easily decomposed by heat, such as hydrogen peroxide vapor, early-formed vapor may be decomposed by the constant heat of vaporizer as it follows a tortuous path through the vaporizer.

Previous low flow rate systems utilized one heater (of one wattage) to preheat the carrier gas prior to its entering the vaporizer. However, when higher air flow rates and higher sterilant injection rates are employed, one heater of one wattage is not sufficient to provide enough heat to the air stream. Furthermore, it may be desirable to provide a wide range of different air flow rates, each requiring a different heating wattage.

Other problems arise when flow-through systems with a high rate of flow are used to decontaminate rigid-walled chambers or enclosures, in which a slightly positive or slightly negative pressure must be maintained, because minute changes in the carrier gas flow rate, produced by adjusting the flow with high velocity blower motors, can be magnified into gross changes in the enclosure pressure, which may exceed process limits or harm processes going on inside the enclosure.

There exists, therefore, a need for further improvements in decontamination systems to accommodate high rates of carrier gas flow-through.

SUMMARY OF THE INVENTION

The present invention provides an optimized method of conducting a closed-loop, flow-through vapor phase decontamination. The invention also provides an improved continuous-operation, closed-loop system for carrying out the method when employing a high carrier gas flow rate.

In the method, a flow of carrier gas is recirculated in a closed-loop conduit circuit that leads into, through, and out of a sealable chamber. The invention can be used for flow rates ranging from only one or two SCFM to flow rates of thousands of SCFM. Preferably, the high flow rates employed in the invention are at least 40 SCFM and, more preferably, between about 40 SCFM and about 70 SCFM. The carrier gas is selectively and controllably heated, in response to the flow rate, to maintain a predetermined carrier gas temperature.

A vaporizer comprising an internal tortuous path, having an entrance and an exit, is provided for vaporizing a liquid decontaminant delivered into a flow of carrier gas through the tortuous path. A plurality of spaced vaporizer heaters, external to the tortuous path, are selectively operated to provide a decreasing heat gradient through the tortuous path from the entrance to the exit, in order to minimize heat degradation of early-formed vapor. The decontaminant vapor is delivered to the chamber via the carrier gas flow entering the chamber and is then converted to a form suitable for disposal after exiting the chamber.

The carrier gas preferably comprises air. The liquid decontaminant preferably comprises aqueous hydrogen peroxide, and the vaporized hydrogen peroxide decontaminant vapor is preferably converted to water and oxygen with a catalytic converter.

To prevent condensation resulting from unacceptable moisture build-up over time, the carrier gas flow is dried before reentering the chamber. However, in the method of the present invention, the carrier gas is partially and selectively dried in response to the monitored temperature, relative humidity, and decontaminant vapor concentration in the chamber. The degree of drying is particularly selected in response to these chamber parameters to maintain a predetermined percent saturation of the decontaminant vapor in the chamber during decontamination.

As a result, the water vapor content or humidity of the carrier gas entering the chamber may be higher (i.e., the carrier gas is dried to a lesser extent) during decontamination than was previously permitted or sought. As mentioned, in the prior closed-loop system disclosed in U.S. Pat. No. 5,173,258, the carrier gas humidity in a closed loop system is continuously reduced to maximize the amount of decontaminant vapor accepted into the carrier gas (or to maximize the decontaminant vapor concentration, rather than the vapor percent saturation).

The selective drying of the carrier gas is preferably carried out by selectively routing a portion of the carrier gas flow through an air dryer positioned upstream of the chamber inlet port and selectively bypassing a remaining portion of the carrier gas flow around the air dryer. The chamber parameters which provide feed-back for selecting the degree of drying can be monitored directly by temperature, relative humidity, and concentration sensors placed in the chamber, or indirectly by other means, as hereinafter described.

The flow-through vapor phase decontamination system of the invention includes a sealable chamber having an inlet port and an outlet port. A conduit circuit is fluidly connected to the chamber ports to provide a closed-loop flow path for recirculating a carrier gas into, through, and out of the chamber. The system also includes a blowing unit and an adjustable drying unit, each fluidly connected to the conduit circuit. The blowing unit serves to push or force the carrier gas around the closed-loop flow path. The adjustable drying unit serves to dry selectively the carrier gas flow entering the chamber.

The drying unit preferably comprises a variable valve having a first flow path and a second flow path, and a regenerative air dryer having an inlet port and an outlet port. The air dryer is positioned downstream of the two-way valve. A first fluid flow line connects the first flow path to the dryer inlet port, while a second fluid flow line bypasses the dryer and connects to the conduit circuit downstream of the drying unit. By varying the amount of flow through the first and second valve flow paths, a selected portion of the carrier gas flow can be routed to bypass the dryer. In this way, the humidity of the carrier gas can be regulated or adjusted (i.e., the carrier gas can be selectively dried) to maintain a predetermined percent saturation of decontaminant vapor in the chamber as the decontamination cycle proceeds.

The blowing unit preferably comprises a first blower positioned upstream and a second blower positioned downstream of the drying unit. More preferably, the blower speed can be adjusted based on feedback from flow sensors to provide a slightly negative or positive pressure within the chamber.

To prevent unwanted gross changes in the chamber pressure, a chamber pressure fine-tuning unit for high flow rate conditions is also provided. The pressure fine-tuning unit comprises an air line fluidly connected to an external source of air and to the closed-loop conduit circuit. A pump and a valve or valves, having an open and a closed position, are fluidly connected to the air line. The flow of carrier gas is recirculated into, through and out of the chamber and around the closed-loop conduit circuit by operating a blower motor. By selectively operating the pump and opening and closing the valve or valves, minute quantities of air can be added to or minute quantities of carrier gas removed from the conduit circuit to maintain a predetermined chamber pressure, in response to monitored chamber pressure readings from a chamber pressure sensor, without changing the speed of the blower.

The system also includes a liquid vaporizer unit for delivering a vaporized liquid decontaminant into the carrier gas flow. The vaporizer unit is fluidly connected to the conduit circuit between the drying unit and the chamber inlet port.

The system includes a heating unit for preheating the carrier gas entering the vaporizer, and comprises a plurality of heaters, preferably of differing wattage, fluidly connected in series and fluidly connected to the carrier gas flow conduit upstream of the vaporizer. By the method of the invention, one or more of the heaters is selectively operated in response to the monitored temperature and flow rate of the carrier gas to maintain a predetermined temperature of the carrier gas flowing through the conduit and into the vaporizer.

In addition, the system includes a converter for converting the decontaminant vapor to a form suitable for disposal, and fluidly connected to the conduit circuit downstream of the chamber outlet port. When the decontaminant vapor is hydrogen peroxide, the converter preferably comprises a catalytic converter for decomposing hydrogen peroxide to water and oxygen.

The system also includes a processing unit for monitoring the following three parameters within the chamber during decontamination: 1) the temperature, 2) the relative humidity, and 3) the vapor concentration. The degree of drying of the carrier gas is selected in response to these three parameters, to maintain a predetermined percent saturation of the decontaminant vapor during decontamination. The processing unit also monitors the chamber pressure.

The processing unit may include a temperature sensor, relative humidity sensor, and a vapor concentration sensor positioned within the chamber to monitor directly the internal chamber temperature, relative humidity, and vapor concentration. Alternatively, the processing unit may include means for indirectly monitoring these parameters, as hereinafter described. The processing unit may also include a pressure sensor to monitor directly the chamber pressure.

BRIEF DESCRIPTION OF THE DRAWINGS

The present invention can be better understood by reference to the drawings in which.

DETAILED DESCRIPTION OF THE INVENTION

The method of the present invention can be used to optimize the efficacy of vapor phase decontamination in a closed, flow-through cycle. The term "decontamination" shall be understood to include sterilization, disinfection, and sanitization. For the purpose of describing the preferred embodiments herein the objective discussed will be sterilization.

The sterilant vapor preferably comprises hydrogen peroxide generated from 30–35% by weight aqueous hydrogen peroxide solution. The carrier gas preferably comprises air. It is contemplated that other condensible gas sterilants and other inert gas carriers, such as nitrogen, may also be used. For purposes of describing the preferred embodiments, the carrier gas and the sterilant vapor discussed will be respectively air and vapor phase hydrogen peroxide generated from an aqueous hydrogen peroxide solution.

In the method, a flow of carrier gas is recirculated in a closed-loop conduit circuit that leads into, through, and out of a sealable sterilization chamber. A liquid sterilant is vaporized and delivered into the carrier gas flow entering the chamber, and then converted to a form suitable for disposal after exiting the chamber, i.e., water and oxygen in the case of hydrogen peroxide sterilant.

The method succeeds in optimizing sterilization by monitoring the chamber temperature, relative humidity, and vapor concentration. The carrier gas is then only partially and selectively dried in response to these parameters to maintain a predetermined percent of sterilant vapor saturation in the sterilization chamber. Percent saturation is defined as the ratio between actual sterilant vapor concentration and the sterilant vapor dewpoint concentration.

In the method of the present invention, the water vapor concentration of the carrier gas entering the chamber may be higher than was previously obtained or desired. Yet, superior kill potentials and more efficient sterilization can be obtained.

Figure 1:
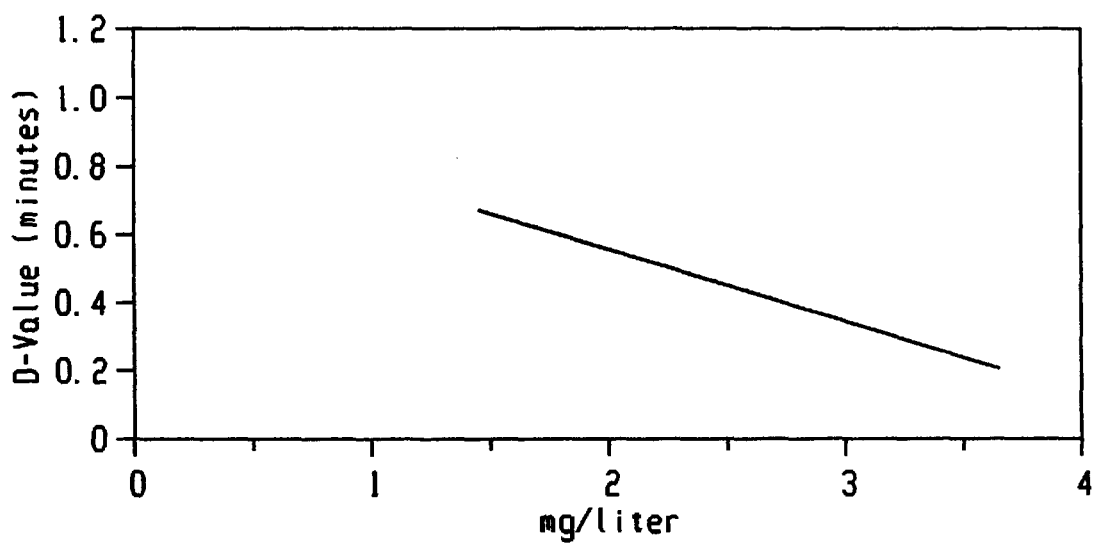
FIG. 1 is a graph showing exemplary D-values of a range of hydrogen peroxide concentrations.
Figure 2:
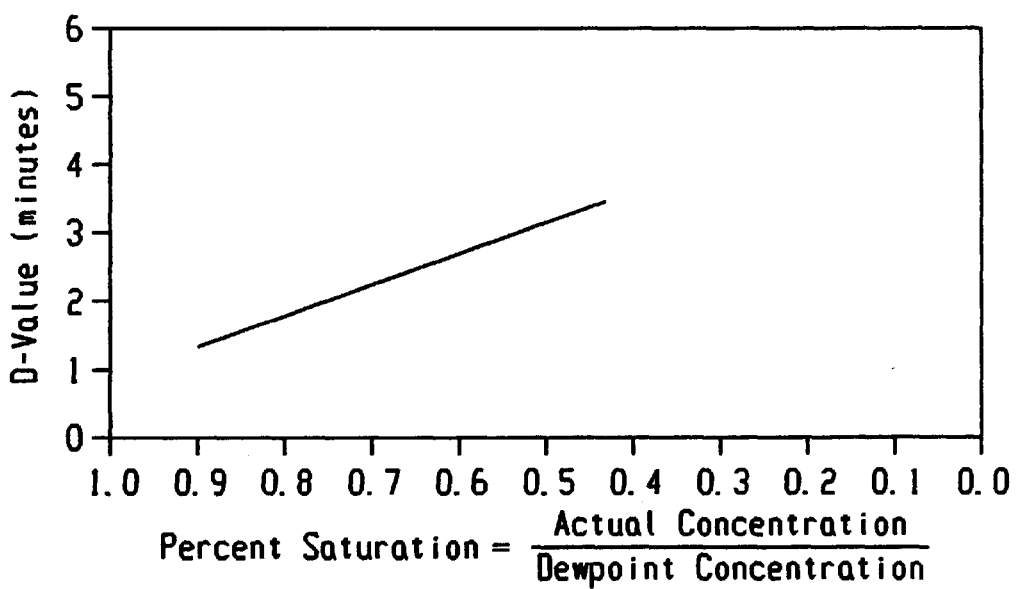
FIG. 2 is a graph showing exemplary D-values of a range of hydrogen peroxide percent saturations.

The improvement provided by the present invention can be appreciated by inspecting FIGS. 1 and 2. FIG. 1 illustrates the relationship between the D-value for *Bacillus stearothermophilus* and hydrogen peroxide sterilant vapor concentrations ranging from 1.5 mg/l to 3.7 mg/l. The percent saturation is held constant at 80%. As indicated, the sterilization efficacy approximately doubles (the D-value is halved) when the concentration is doubled.

Prior closed, flow-through systems recognized the foregoing relationship and attempted to maximize the concentration of sterilant vapor in the carrier gas flowing into the sterilization chamber. The amount of sterilant that can be injected into a carrier gas is limited, however, by dew point considerations. Table I shows the dewpoint concentrations for 35% hydrogen peroxide that is flash vaporized (as described in U.S. Pat. No. 4,642,165, incorporated by reference herein) into an enclosure with the given temperature and relative humidity air:

TABLE 1

| Enclosure Temperature | Dewpoint Concentration for $H_2O_2$ Vapor |  |  |  |
|---|---|---|---|---|
| | Enclosure Relative Humidity | | | |
| | 0% | 10% | 20% | 30% |
| 15° C. | 1.103 | 0.903 | 0.731 | 0.585 |
| 20° C. | 1.562 | 1.284 | 1.044 | 0.839 |
| 25° C. | 2.184 | 1.805 | 1.477 | 1.185 |
| 30° C. | 3.008 | 2.497 | 2.051 | 1.651 |
| 35° C. | 4.097 | 3.410 | 2.810 | 2.270 |
| 40° C. | 5.485 | 4.599 | 3.803 | 3.081 |

FIG. 2 illustrates the relationship between the D-value for *Bacillus stearothermophilus* and hydrogen peroxide vapor percent saturations ranging from 40 to 90%. The hydrogen peroxide vapor concentration is maintained at 1.6 mg/l. As indicated, the sterilization efficacy nearly quadruples (the D-value goes from 4 to almost 1) when the sterilant vapor percent saturation is slightly more than doubled. By controlling percent saturation independently of concentration, the present invention obtains significantly improved sterilization.

Figure 3:
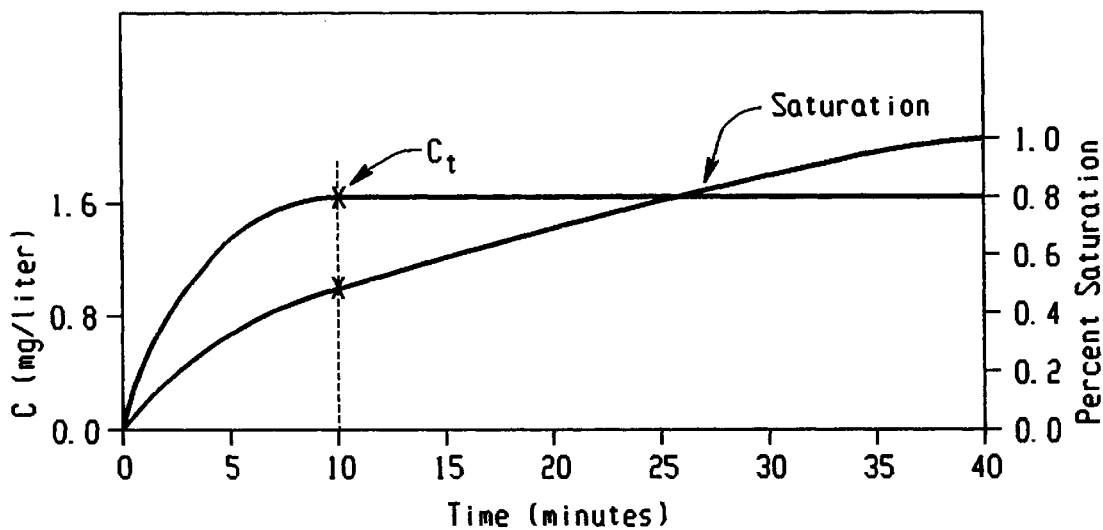
FIG. 3 is a graph showing the sterilant concentrations and sterilant percent saturations over a sterilization cycle for a prior closed, flow-through prior sterilization method, which maintains a predetermined sterilant vapor concentration.
Figure 4:
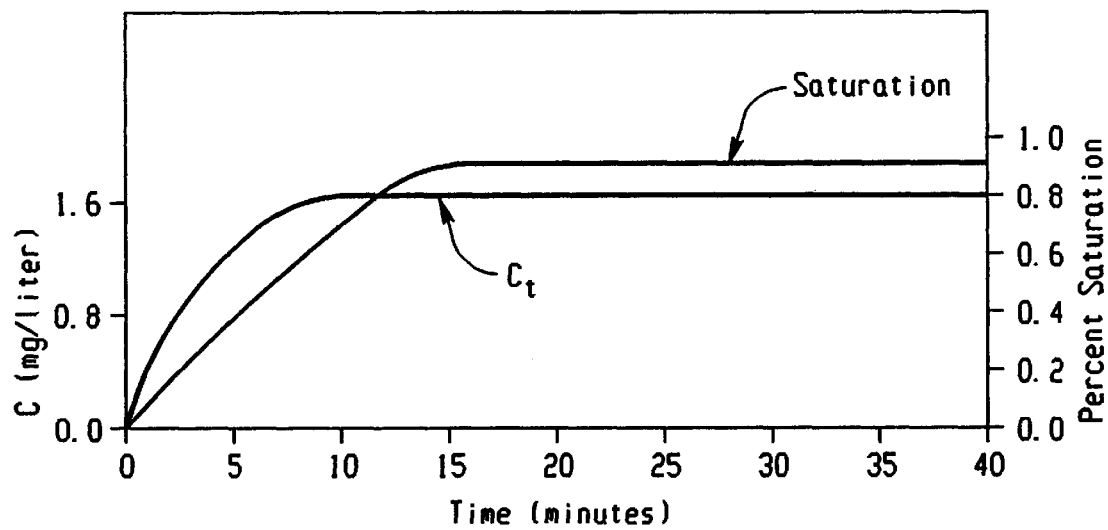
FIG. 4 is a graph showing the sterilant concentrations and sterilant percent saturations over a sterilization cycle for the sterilization method of the present invention, which maintains a predetermined sterilant vapor percent saturation.
Figure 5:
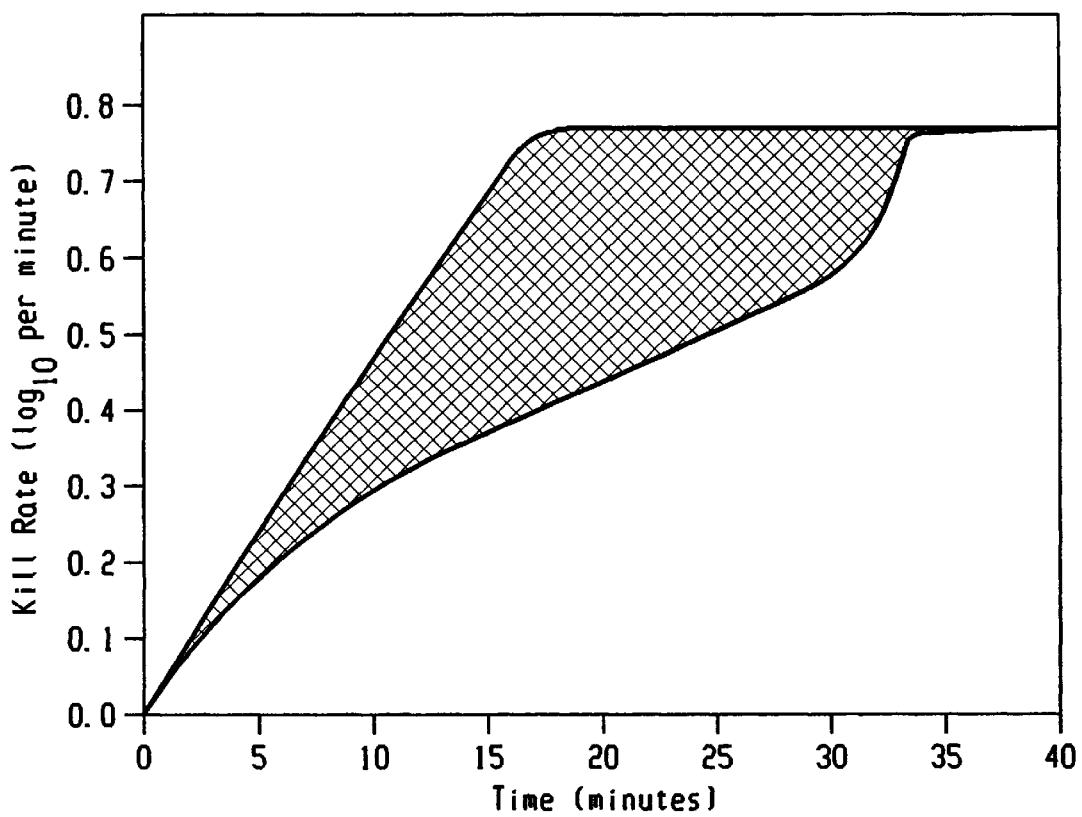
FIG. 5 is a graph comparing the bacterial kill rates over a sterilization cycle for the sterilization methods of FIGS. 3 and 4.

FIGS. 3–5 also illustrate the improved results obtained with the present invention. FIG. 3 illustrates a typical sterilant vapor and percent saturation plot for a prior sterilization cycle which seeks to maximize concentration. FIG. 4 illustrates a typical sterilant vapor and percent saturation plot for the present invention. The percent saturation is below 70% during the first half of the prior sterilization cycle. In the present invention, the percent saturation is only below 70% for the first ten minutes of the sterilization cycle and is at about 90% for most of the cycle.

The kill potential for a sterilization cycle can be determined by plotting the instantaneous kill rate versus time for a sterilization cycle and calculating the area under the curve. Using the D-values from FIG. 2 and the curves from FIGS. 3 and 4, the kill rates for the prior system and the present invention are plotted in FIG. 5. The cross-hatch area shows the significantly improved kill potential for the present invention.

Figure 6:
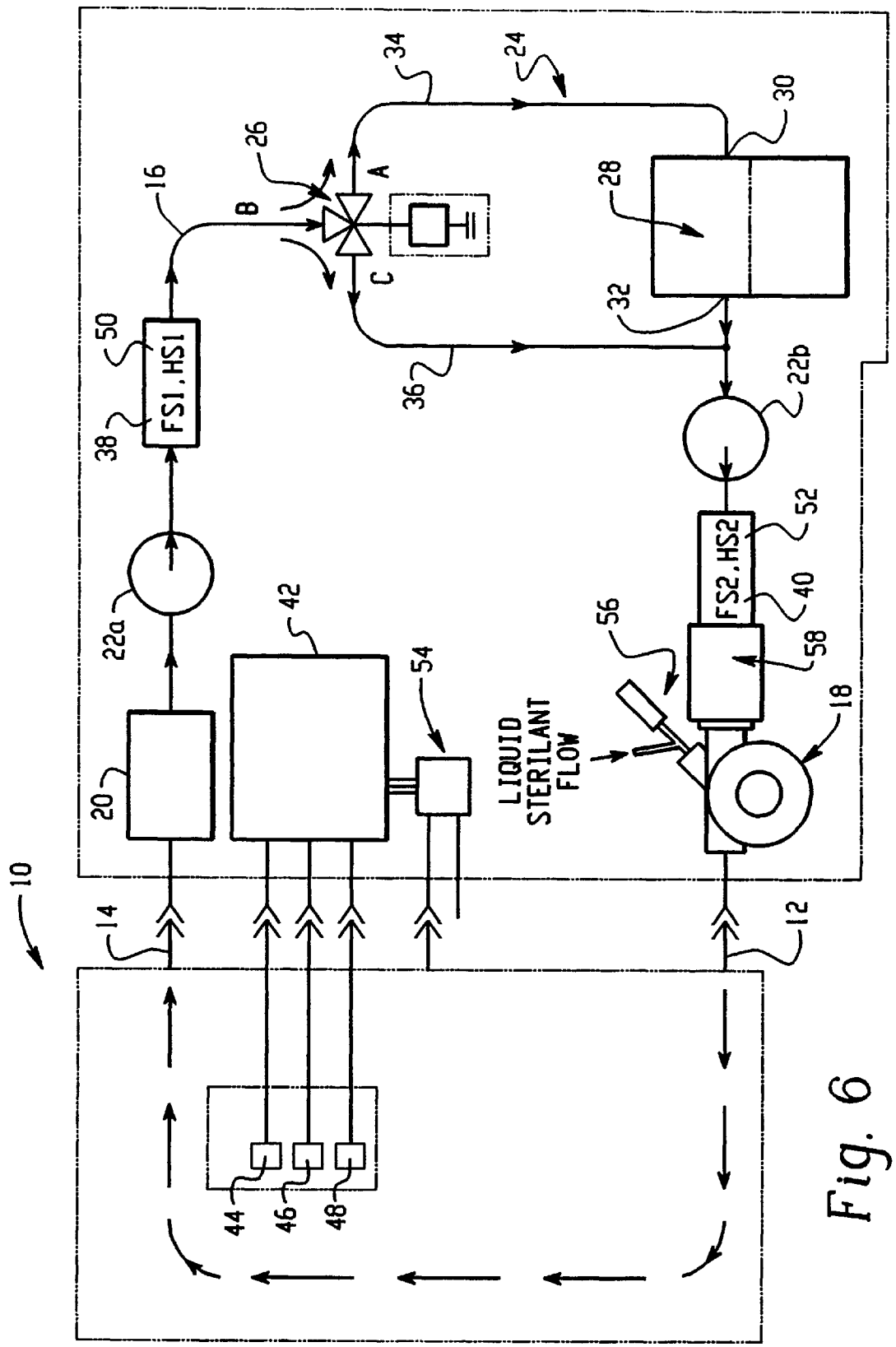
FIG. 6 is a schematic illustration of one embodiment of the continuous-operation, closed-loop flow through system of the present invention.

The method of the invention will now be described with further reference to the exemplary system illustrated in FIG. 6. As shown, the flow-through vapor phase sterilization system of the invention includes a sealable chamber 10 having an inlet port 12 and an outlet port 14. A conduit circuit 16 is fluidly connected to the chamber ports to provide a closed-loop flow path for recirculating a carrier gas into, through, and out of the chamber 10.

The system also includes a liquid sterilant vaporizer unit 18 for delivering a vaporized liquid sterilant into the carrier gas flow. The vaporizer unit 18 is fluidly connected to the conduit circuit between the drying unit and the chamber inlet port. Liquid sterilant is preferably atomized in an atomizer 56 fluidly connected to the vaporizer 18 and delivered to the vaporizer in the form of a fine mist to increase the likelihood of complete vaporization.

Figure 7:
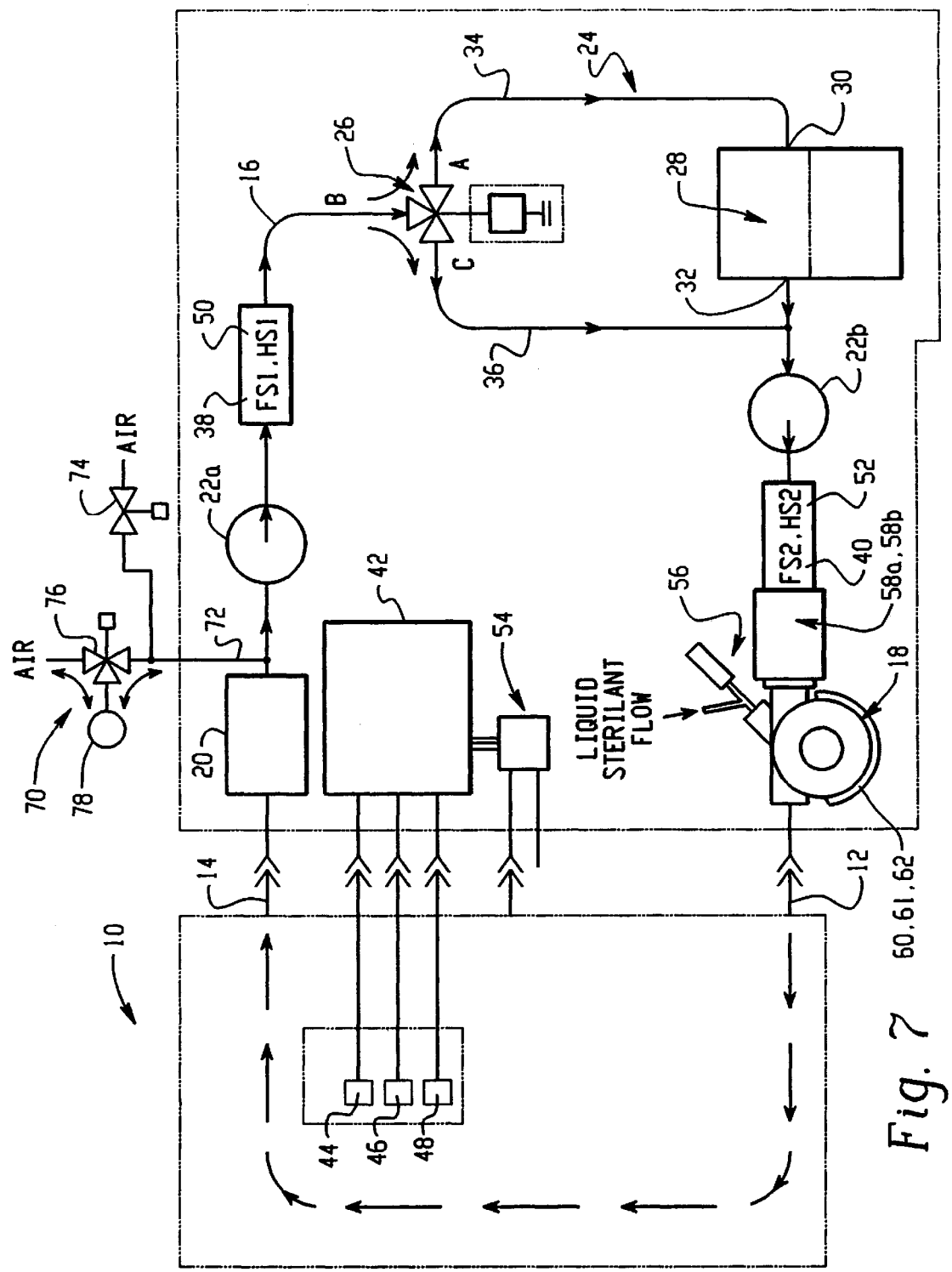
FIG. 7 is a schematic illustration of another embodiment of the continuous-operation, closed-loop flow through system of the present invention.
Figure 8:
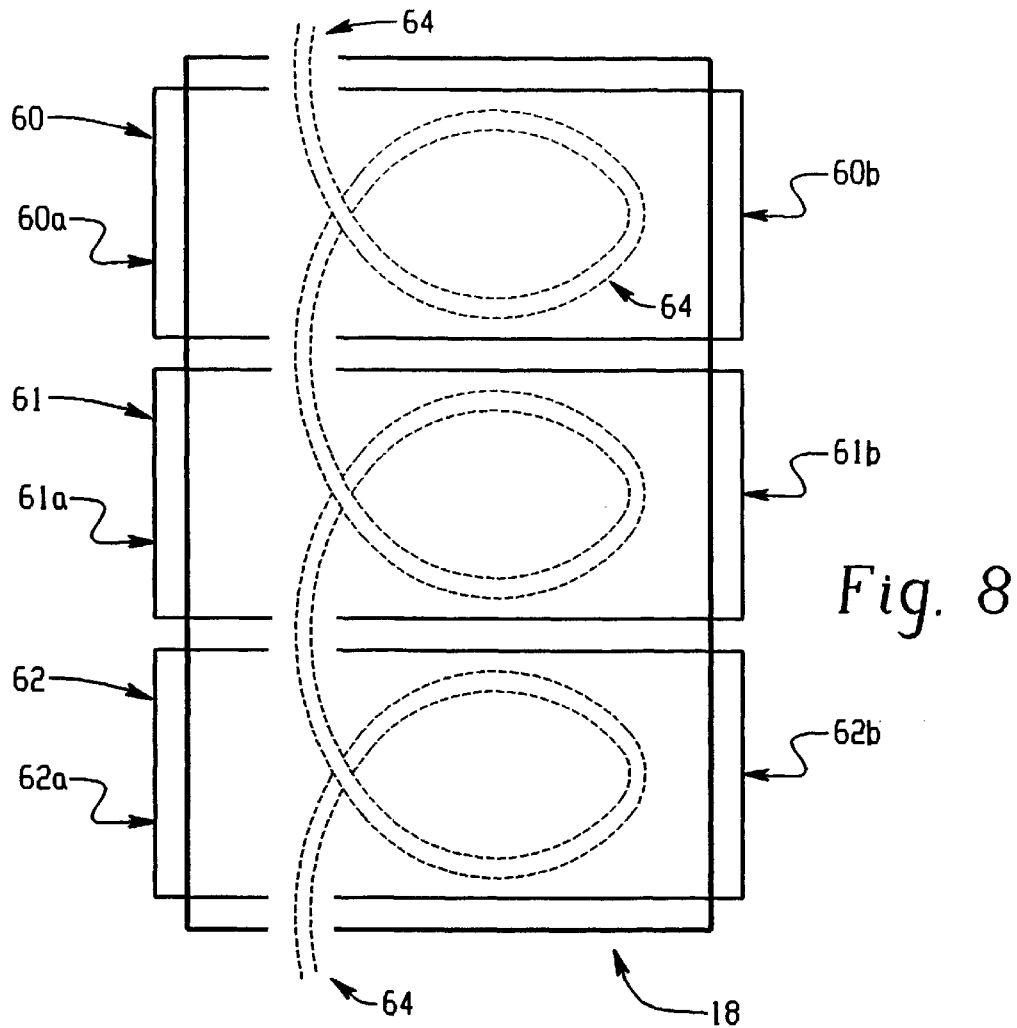
FIG. 8 is a schematic illustration of the liquid decontaminant vaporizer, including vaporizer heaters.

As illustrated in FIGS. 7 and 8, a series of spaced vaporizer heaters 60, 61, 62 of decreasing wattage are preferably employed to provide a heat gradient from the top to the bottom of the vaporizer 18 when a heat-sensitive vapor, such as hydrogen peroxide vapor, is the sterilant. Most of the flash vaporization of the liquid/mist sterilant occurs at the top of the tortuous path 64 of the vaporizer. As the liquid/vapor mixture descends through the tortuous path, heaters of lower wattage provide less heat at the middle and bottom of the vaporizer, so as not to degrade already-formed vapor, and to vaporize any remaining liquid. Preferably, the heaters are spaced and controllable in groups of two (60a and 60b; 61a and 61b; 62a and 62b). For example, when there is a high rate of flow of air and vapor through the vaporizer, all the heaters may be on. When there is a low rate of flow, some of the heaters may selectively be turned off.

In addition, the system includes a converter 20 for converting the sterilant vapor to a form suitable for disposal, and fluidly connected to the conduit circuit downstream of the chamber outlet port 14. When the sterilant vapor is hydrogen peroxide, the converter 20 preferably comprises a catalytic converter for decomposing hydrogen peroxide to water and oxygen.

The system also includes a blowing unit 22a and 22b and an adjustable drying unit 24, each fluidly connected to the conduit circuit. The blowing unit serves to push or force the carrier gas around the closed-loop flow path. As illustrated in FIG. 7 and described further below, the system includes an additional chamber pressure fine-tuning unit 70, fluidly connected to the conduit circuit, that may be used to fine-tune the pressure in flow path by adding minute quantities of atmospheric air or removing minute quantities of the carrier gas in the conduit circuit. This unit is preferably employed when carrier gas flows having high flow rates are used and the unit may be used to fine-tune the pressure in the enclosure without changing the speed of the blowers of the blowing unit.

Figure 9:
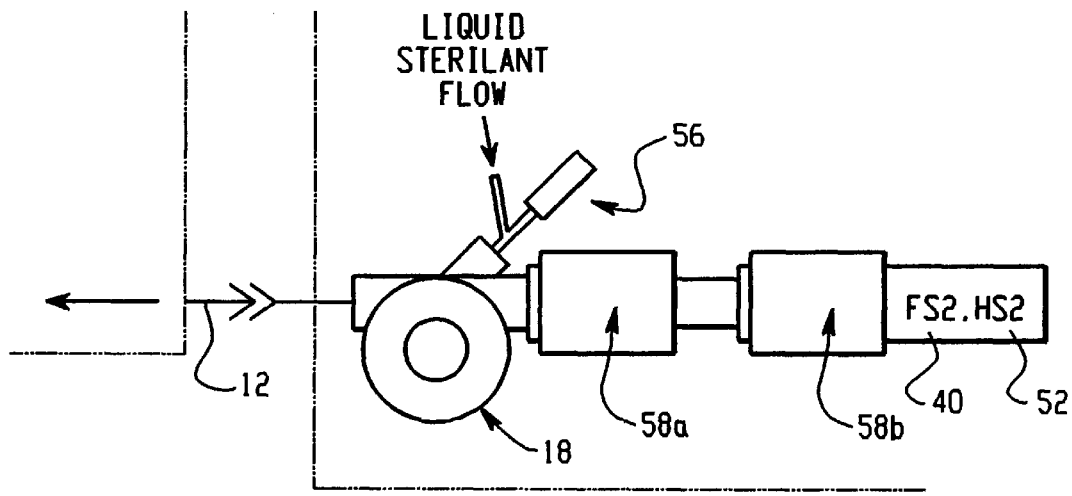
FIG. 9 is a cutaway portion of the illustration of FIGS. 7 and 8, schematically illustrating the carrier gas preheaters in series.

At least one heater 58 is fluidly connected to the conduit circuit downstream from the drying unit for controlling the temperature of the carrier gas entering the vaporizer 18. As illustrated in FIGS. 7 and 9, preferably at least two heaters 58a and 58b of different wattage, fluidly connected in series, are provided. The heaters are independently controllable by the processing unit 42 (described below), based on the sensed carrier gas flow rate by the flow sensor 40 and the known rate of sterilant injection into the vaporizer. Therefore, the heaters can selectively be activated to preheat the carrier gas to a desired temperature. For example, in low flow rate conditions (less than 20 SCFM) and/or low injection rates, a low wattage heater is selectively turned on. In medium flow rate conditions (20–40 SCFM) and/or injection rates, a higher wattage heater may be selectively used. In higher flow rate conditions (40–70 SCFM), a combination of high and low wattage heaters may be selectively used. The heaters may also be pulsed on and off by the processor, in response to a sensed temperature by temperature sensor 44, to maintain a desired temperature of the carrier gas.

The adjustable drying unit 24 serves to dry selectively the carrier gas flow entering the chamber. The drying unit preferably comprises a variable valve 26 having a first flow path A–B and a second flow path B–C, and a regenerative air dryer 28 having an inlet port 30 and an outlet port 32. The air dryer 28 is positioned downstream of the variable valve 26. A first fluid flow line 34 connects the first flow path to the dryer inlet port 30, while a second fluid flow line 36 bypasses the dryer 28 and connects to the conduit circuit downstream of the drying unit. By varying the amount of flow through the first and second valve flow paths, a selected portion of the carrier gas flow can be routed to bypass the dryer 28. In this way, the humidity of the carrier gas can be regulated or adjusted (i.e., the carrier gas can be selectively dried) to maintain a predetermined percent saturation of sterilant vapor in the chamber as the sterilization cycle proceeds.

A first humidity sensor 50 is positioned downstream of the converter 20 to measure the absolute humidity of the air flow exiting the converter 20. A second humidity sensor 52 is positioned downstream of the air dryer 28 to measure the absolute humidity of the air flow exiting the air dryer 28. Assuming, for example, that the air stream exiting the converter has a humidity of 11.5 mg/l and the air dryer reduces the humidity of the air stream that passes through it to 2.3 mg/l, the humidity of the air stream entering the vaporizer can be calculated as reported in Table 2.

TABLE 2

| Fraction Bypassed | Fraction Dried | Air Stream Absolute Humidity (Humidity Sensor 52 reading) | |
|---|---|---|---|
| 0 | 1.0 | 2.3 | mg/liter |
| .1 | .9 | 3.22 | mg/liter |
| .2 | .8 | 4.14 | mg/liter |
| .3 | .7 | 5.06 | mg/liter |
| .4 | .6 | 5.98 | mg/liter |
| .5 | .5 | 6.9 | mg/liter |
| .6 | .4 | 7.82 | mg/liter |
| .7 | .3 | 8.74 | mg/liter |
| .8 | .2 | 9.66 | mg/liter |
| .9 | .1 | 10.58 | mg/liter |
| 1.0 | 0 | 11.5 | mg/liter |

The blowing unit preferably comprises a first blower 22a positioned upstream and a second blower 22b positioned downstream of the drying unit. More preferably, the blowers can be adjusted based on feedback from flow sensors 38 and 40 to provide a slightly negative or positive pressure within the sterilization chamber 10 as monitored by a pressure transducer 54.

The chamber pressure fine-tuning unit 70, illustrated in FIG. 7, preferably comprises an air line 72, positioned upstream of blower 22a, fluidly connecting the conduit circuit to atmospheric air via two-way valve 74 and three-way valve 76. Three-way valve 76 is fluidly connected to a pump 78. When the pressure adjusting unit is not being used, valve 74 is closed and valve 76 is toggled to be closed to the carrier gas stream in the conduit circuit. When a minute quantity of carrier gas is to be removed from the carrier gas stream, valve 76 is toggled to the carrier gas stream path and pump 78 withdraws a small amount of air from the process air stream. When a minute quantity of atmospheric air is to be added to the carrier gas stream, valve 76 is closed and valve 74 is momentarily opened. The adding and removing processes may be continued in a see-saw fashion until the point of desired enclosure pressure is reached, at which time the pressure fine-tuning unit is deactivated. The activation or deactivation of the unit is processor controlled based on feedback from at least pressure sensor 54.

In addition, the system includes a processing unit 42 for monitoring the following three parameters within the sterilization chamber during sterilization: 1) the temperature, 2) the relative humidity, and 3) the sterilant vapor concentration. The processing unit also determines or selects the degree of drying of the carrier gas in response to these three parameters, to maintain a predetermined percent saturation of the sterilant vapor during sterilization.

The processing unit may include a temperature sensor 44, relative humidity sensor 46, and a vapor concentration sensor 48 positioned within the chamber 10 to monitor directly the internal chamber temperature, relative humidity, and vapor concentration. Alternatively, the processing unit may include means for monitoring these parameters indirectly. The vapor concentration can be indirectly monitored through calculations based on the measured air-flow rate and sterilant vapor injection rate. The relative humidity can be indirectly monitored by using the humidity sensor 50 positioned downstream of the converter to measure the absolute humidity of the exiting air flow. The background humidity is subtracted from that value. A standard water vapor dew point chart can then be consulted to provide the relative humidity for the difference at the chamber temperature.

Preferred embodiments of the invention are further illustrated by the following examples, in which an aqueous 35% hydrogen peroxide solution was flash vaporized:

EXAMPLE 1

The chamber temperature is 35° C., relative humidity is 20%, and sterilant vapor concentration is 2.27 mg/l. Reference to Table I or another available dewpoint concentration chart shows that the sterilant dewpoint concentration is 2.810 mg/l. The percent saturation is therefore 80%.

According to the present invention, the humidity of the carrier gas entering the chamber is adjusted by repositioning the variable valve to bypass a larger fraction of air so that the relative humidity of the enclosure becomes 30%. According to the dewpoint concentration chart, the dewpoint concentration is now 2.27 mg/l. The percent saturation then becomes 100%.

EXAMPLE 2

The chamber temperature is 40° C. and the sterilant vapor concentration is 3.081 mg/l, calculated based on the air flow rate and the sterilant delivery rate. Humidity sensor 50 indicates that the absolute humidity in the returning air stream is 15.94 mg/l. For the flash vaporized sterilant, the aqueous solution contributes 10.22 mg/l humidity or (65/35)×3.081 mg/l. Subtracting this value from the absolute humidity results in 15.94−5.72 mg/l=10.22 mg/l background humidity. Referring to a dewpoint chart, at 40° C. this results in 20% relative humidity. At 40° C. and 20% relative humidity the sterilant vapor dewpoint concentration is 3.803 mg/l. This means that the calculated percent saturation is 81%.

The variable valve is repositioned to bypass a larger fraction of air flow around the air dryer. The background humidity in the returning air stream at dewpoint conditions at 40° C. for a 3.081 mg/l hydrogen peroxide vapor concentration according to Table 1 is 30%. The absolute humidity corresponding to a 30% background relative humidity is found as follows:

$$AH=(65/35)\times 3.081 \text{ mg/l plus } 15.35 \text{ mg/l}=21.08 \text{ mg/l}.$$

Repeating the above calculations for the new absolute humidity show that the percent saturation is 100%. Thus, by increasing the carrier gas humidity from 20% to 30% the chamber reaches 100% sterilization, greatly improving the sterilization.

EXAMPLE 3

Blower 22b is adjusted based on feedback from the flow sensor 40 to provide an air flow rate of 50 CFM. Blower 22b is adjusted to provide a lower air flow rate. The rotational speed of blower 22a is increased (or decreased) based upon the reading from the pressure transducer 54. A slightly positive (0.2 in WC $\leq$ P $\leq$ 2 in WC) pressure is thus maintained in the semi-sealed enclosure while maintaining the desired air flow rate, sterilant vapor concentration and percent saturation.

EXAMPLE 4

Blower 22a is adjusted based on feedback from the flow sensor 38 to provide an air flow rate of 50 CFM. Blower 22b is adjusted to provide a lower air flow rate. The rotational speed of blower is increased (or decreased) based upon the reading from the pressure transducer 54. A slightly negative (02 in WC $\leq$ P $\leq$ −0.13 in WC) pressure is thus maintained in the semi-sealed enclosure while maintaining the desired air flow rate, sterilant vapor concentration and percent saturation.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

We claim:

1. A method for heating a carrier gas entering a vaporizer in a flow-through decontamination system, the vaporizer having an internal tortuous path defined within the vaporizer, the tortuous path having an entrance and an exit, a carrier gas conduit connected to the entrance of the tortuous path, and a plurality of heaters mounted to the carrier gas conduit and the tortuous path, the method comprising:

flowing a carrier gas from the carrier gas conduit into the tortuous path entrance of the vaporizer;

within the tortuous path, vaporizing a liquid sterilant and entraining the vaporized liquid sterilant into the flowing carrier gas to form a gaseous sterilant flowing through the tortuous path;

monitoring a temperature and a flow rate of the carrier gas;

selectively operating the heaters in response to the monitored temperature and flow rate to maintain a predetermined temperature of at least the carrier gas flowing through the carrier gas conduit to the vaporizer tortuous path entrance, whereby a predetermined vapor absorbing capacity of the carrier gas is maintained.

2. The method of claim 1 wherein the gaseous sterilant includes hydrogen peroxide vapor.

3. The method of claim 1 wherein the carrier gas is air.

4. The method of claim 1 wherein the plurality of heaters are controllably operated in groups of two.

5. The method of claim 1 further including:

flowing the carrier gas and the entrained, vaporized liquid sterilant into a chamber;

flowing the carrier gas and any remaining vaporized liquid sterilant from the chamber back to the carrier gas conduit in a closed loop.

6. The method of claim 5 further including:
removing the remaining vaporized liquid sterilant from the returned carrier gas prior to flowing the carrier gas into the tortuous path entrance.

7. The method of claim 6 further including:
monitoring an increase in chamber pressure or a decrease in chamber pressure in the chamber;
in response to monitoring said increase in chamber pressure, removing carrier gas from the conduit; and
in response to monitoring said decrease in chamber pressure, adding carrier gas to the conduit.

8. The method of claim 1 wherein the plurality of heaters are operated at different temperatures to maintain a temperature gradient over the tortuous path.

9. A method of heating carrier gas comprising:
flowing carrier gas from a supply conduit to a tortuous path of a vaporizer;
vaporizing a liquid sterilant and entraining the vaporized liquid sterilant in the carrier gas in the tortuous path;
supplying the carrier gas with the entrained vaporized liquid sterilant to a chamber;
heating the carrier gas to maintain a preselected, non-constant thermal profile from the supply conduit through the tortuous path to the chamber.

10. A method of heating carrier gas comprising:
flowing carrier gas from a supply conduit to a tortuous path defined within a vaporizer;
vaporizing a liquid sterilant and entraining the vaporized liquid sterilant in the carrier gas in the tortuous path;
supplying the carrier gas with the entrained vaporized liquid sterilant to a chamber;
heating the carrier gas to maintain a preselected, non-constant thermal profile, the thermal profile including a preselected decreasing thermal gradient between the supply conduit and the chamber.

11. An apparatus for heating a carrier gas entering a vaporizer in a flow-through decontamination system, the apparatus comprising:
a vaporizer comprising an internal tortuous path defined within the vaporizer, the tortuous path having an entrance and an exit, the vaporizer receiving a liquid sterilant, vaporizing the liquid sterilant, and entraining the vaporized liquid sterilant into a carrier gas along the tortuous path to form a gaseous sterilant;
a carrier gas conduit connected to the entrance of the tortuous path within the vaporizer;
a plurality of heaters, at least one of the heaters mounted to the conduit for heating the carrier gas flowing through the heaters and the conduit;
a processing unit for monitoring the temperature and flow rate of the carrier gas through the conduit and for selectively operating one or more of the heaters in response to the monitored temperature and flow rate to maintain a predetermined temperature of the carrier gas flowing through the conduit.

12. The apparatus of claim 11, wherein each of the plurality of heaters has a different wattage.

13. The apparatus of claim 11 wherein the processing unit includes:
a temperature sensor in communication with the vaporizer tortuous path to provide a signal representative of a temperature of the carrier gas flowing therethrough; and
a controller for adjusting at least one of the plurality of heaters based upon the signal from the temperature sensor.

14. The apparatus of claim 11 wherein the plurality of heaters includes at least two heaters mounted along the tortuous path for heating the carrier gas flowing therethrough.

15. An apparatus for heating a carrier gas entering a vaporizer in a flow-through decontamination system, the apparatus comprising:
a vaporizer comprising an internal tortuous path having an entrance and an exit, the vaporizer receiving a liquid sterilant, vaporizing the liquid sterilant, and entraining the vaporized liquid sterilant into a carrier gas along the tortuous path to form a gaseous sterilant;
a carrier gas conduit connected to the entrance of the tortuous path;
a plurality of heaters, at least one of the heaters mounted to the conduit for heating the carrier gas flowing through the heaters and the conduit;
a processing unit for monitoring the temperature and flow rate of the carrier gas through the conduit and for selectively operating one or more of the heaters in response to the monitored temperature and flow rate to maintain a predetermined temperature of the carrier gas flowing through the conduit, the processing unit including a flow sensor in communication with the entrance of the vaporizer to provide a signal representative of a flow rate of the carrier gas through the entrance of the tortuous path; and a controller for adjusting at least one of the plurality of heaters based upon the signal from the flow sensor.

16. An apparatus for heating a carrier gas entering a vaporizer in a flow-through decontamination system, the apparatus comprising:
a vaporizer comprising an internal tortuous path having an entrance and an exit, the vaporizer receiving a liquid sterilant, vaporizing the liquid sterilant, and entraining the vaporized liquid sterilant into a carrier gas along the tortuous path to form a gaseous sterilant;
a carrier gas conduit connected to the entrance of the tortuous path;
a plurality of heaters, at least one of the heaters mounted to the conduit for heating the carrier gas flowing through the heaters and the conduit;
a processing unit for monitoring the temperature and flow rate of the carrier gas through the conduit;
a means for introducing sterilant to the entrance of the vaporizer; and
a controller for adjusting at least one of the plurality of heaters depending upon the rate of sterilant introduction to the vaporizer.

17. An apparatus for heating a carrier gas entering a vaporizer in a decontamination system, the apparatus comprising:
a vaporizer including an internal tortuous path having an entrance and an exit, the vaporizer receiving a liquid sterilant, vaporizing the liquid sterilant, and entraining the vaporized liquid sterilant into a carrier gas along the tortuous path to form a gaseous sterilant;
a carrier gas conduit connected to the entrance of the tortuous path;
a plurality of heaters, at least one of the heaters disposed proximate to the conduit for heating the carrier gas flowing through the heaters and the conduit;
a processing unit for monitoring the temperature and flow rate of the carrier gas through the conduit and for selectively operating one or more of the heaters to maintain a predetermined temperature of the carrier gas flowing through the conduit;

a sterilization chamber having an inlet connected with the vaporizer tortuous path and an outlet connected with the carrier gas conduit such that the carrier gas flows in a closed loop;

a pressure sensor for sensing carrier gas pressure; and a means for adding and removing carrier gas from the carrier gas conduit in response to changes in the sensed carrier gas pressure.

18. An apparatus for heating a carrier gas entering a vaporizer in a flow-through decontamination system, the apparatus comprising:

a vaporizer comprising an internal tortuous path defined within the vaporizer, the tortuous path descending from an entrance at a top to an exit at a bottom, the vaporizer receiving a liquid sterilant, vaporizing the liquid sterilant, and entraining the vaporized liquid sterilant into a carrier gas along the tortuous path to form a gaseous sterilant;

a carrier gas conduit connected to the entrance of the tortuous path;

a plurality of heaters, including:

(1) at least one heater mounted to the conduit for heating the carrier gas flowing through the heaters and the conduit, and (2) at least two heaters mounted along the tortuous path in the vaporizer for heating the carrier gas flowing therethrough;

a processing unit for:

(1) monitoring (I) a temperature and (ii) a flow rate of the carrier gas and (2) selectively controlling the at least two heaters to maintain a preselected thermal gradient in the carrier gas between the top and the bottom of the tortuous path.

* * * * *